United States Patent [19]

Berg

[11] Patent Number: 5,425,854
[45] Date of Patent: Jun. 20, 1995

[54] SEPARATION OF METHYLENE CHLORIDE FROM TETRAHYDROFURAN BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 373,549

[22] Filed: Jan. 17, 1995

[51] Int. Cl.⁶ .................. B01D 3/40; C07C 17/38; C07D 307/08
[52] U.S. Cl. .................. 203/57; 203/58; 203/60; 203/62; 203/63; 203/64; 549/429; 570/262
[58] Field of Search ........... 203/63, 60, 64, 62, 203/57, 58, 59; 570/262; 549/429

[56] References Cited

U.S. PATENT DOCUMENTS

| | | | |
|---|---|---|---|
| 2,481,211 | 9/1949 | Fugua | 203/63 |
| 2,500,329 | 3/1950 | Steitz | 203/70 |
| 2,528,761 | 11/1950 | Lake et al. | 203/69 |
| 2,575,285 | 11/1951 | Carlson et al. | 203/63 |
| 2,617,757 | 11/1952 | Michael | 203/69 |
| 3,329,585 | 7/1967 | Huxtable | 549/429 |
| 3,410,760 | 11/1968 | Craig et al. | 549/429 |
| 5,051,153 | 9/1991 | Berg | 570/262 |
| 5,124,005 | 6/1992 | Berg et al. | 570/262 |
| 5,310,954 | 5/1994 | Hiles | 549/429 |

FOREIGN PATENT DOCUMENTS 59-76026  4/1984  Japan .................. 570/262

*Primary Examiner*—Wilbur Bascomb, Jr.

[57] ABSTRACT

Methylene chloride is difficult to separate from tetrahydrofuran by conventional distillation or rectification because of the proximity of their vapor pressures. Methylene chloride can be readily separated from tetrahydrofuran by extractive distillation. Effective agents are 1-pentanol, 1,2-butanediol and 3-nitrotoluene.

1 Claim, No Drawings

SEPARATION OF METHYLENE CHLORIDE FROM TETRAHYDROFURAN BY EXTRACTIVE DISTILLATION

FIELD OF THE INVENTION

This invention relates to a method for separating methylene chloride from tetrahydrofuran using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuous removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

| Effect of Relative Volatility an Theoretical Stage Requirements. | | | | | | | | |
|---|---|---|---|---|---|---|---|---|
| Separation Purity, | Relative Volatility | | | | | | | |
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 97 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Methylene chloride boils at 40° C., tetrahydrofuran boils at 65° C. and the vapor-liquid ratio might be expected to be about 1.65 and thus be easy to separate by conventional rectification. However the vapor-liquid equilibrium ratio is not uniform. While no azeotrope exists between these two, there is a pinch point at about 5% methylene chloride at which the relative volatility is only 1.15. Table 1 shows that at this relative volatility, separation by rectification becomes difficult. Extractive distillation would be an attractive method of effecting the separation of methylene chloride from tetrahydrofuran if agents can be found that (1) will create a large apparent relative volatility between methylene chloride and tetrahydrofuran and (2) are easy to recover from tetrahydrofuran. Table 2 shows the relative volatility required to obtain 99% purity. With no agent, 88 actual plates are required. With an agent giving a relative volatility of 2.3, only 15 actual plates are required.

TABLE 2

| Theoretical And Actual Plates Required vs. Relative Volatility For Methylene Chloride - Tetrahydrofuran Separation | | |
|---|---|---|
| Relative Volatility | Theoretical Plates Required At Total Reflux, 99% Purity | Actual Plates Required 75% Efficiency |
| 1.15 | 66 | 88 |
| 1.7 | 17 | 23 |
| 2.3 | 11 | 15 |

OBJECTIVE OF THE INVENTION

The object of this invention is to provide a process or method of extractive distillation that will enhance the relative volatility of methylene chloride from tetrahydrofuran in their separation in a rectification column. It is a further object of this invention to identify organic compounds which in addition to the above constraints, are stable, can be separated from tetrahydrofuran and recycled to the extractive column with little decomposition.

SUMMARY OF THE INVENTION

The objects of this invention are to provide a process for separating methylene chloride from tetrahydrofuran which entails the use of certain organic compounds as the agent in extractive distillation.

DETAILED DESCRIPTION OF THE INVENTION

I have discovered that certain organic compounds will greatly improve the relative volatility of methylene chloride from tetrahydrofuran and permit the separation of methylene chloride from tetrahydrofuran by rectification when employed as the agent in extractive distillation. Table 3 lists the compounds that I have found to be effective. They are

TABLE 3

| Effective Extractive Distillation Agents For Separating Methylene Chloride From Tetrahydrofuran | |
|---|---|
| Compounds | Relative Volatility |
| None | 1.15 |
| Ethylene glycol | 1.65 |
| 1,2-Butanediol | 2.2 |
| 1,3-Butanediol | 2.2 |
| 1,4-Butanediol | 1.7 |
| 2,3-Butanediol | 2.0 |
| Dipropylene glycol | 1.6 |
| 1,5-Pentanediol | 1.6 |
| 3-Methyl-2,4-pentanediol | 1.9 |
| 2-Methyl-1,3-propanediol | 1.75 |
| 1,2,6-Trihydroxyhexane | 1.75 |
| 2-Hydroxyacetophenone | 1.65 |
| Benzyl benzoate | 1.55 |
| Butyl lactate | 1.55 |
| Phenyl acetate | 1.65 |
| Butyronitrile | 1.5 |
| Methyl ethyl ketoxime | 2.0 |
| Methyl isobutyl ketoxime | 1.5 |
| Ethyl caproate | 1.5 |
| Ethyl isovalerate | 1.6 |

TABLE 3-continued

Effective Extractive Distillation Agents For Separating Methylene Chloride From Tetrahydrofuran

| Compounds | Relative Volatility |
|---|---|
| Butyl aldehyde oxime | 2.5 |
| Methyl valerate | 1.7 |
| Methyl benzoate | 1.7 |
| Benzonitrile | 1.85 |
| Isopropyl lactate | 1.55 |
| Isoamyl formate | 1.65 |
| Butyl formate | 1.55 |
| Butyl butyrate | 1.55 |
| Tri-2-ethyl hexyl trimellitate | 1.5 |
| Propylene carbonate | 1.55 |
| 2-Undecanone | 1.5 |
| Diisobutyl ketone | 1.55 |
| 2,6-Dimethyl-4-heptanone | 1.6 |
| Acetophenone | 1.7 |
| Nitromethane | 1.7 |
| Nitroethane | 1.9 |
| 1-Nitropropane | 1.9 |
| 2-Nitropropane | 1.65 |
| Nitrobenzene | 1.75 |
| 2-Nitrotoluene | 1.75 |
| 3-Nitrotoluene | 2.2 |
| Methyl n-amyl ketoxime | 1.95 |
| Acetonitrile | 1.55 |
| Butyronitrile | 1.5 |
| Tridecyl alcohol | 1.5 |
| 1-Decanol | 1.6 |
| Isodecyl alcohol | 1.95 |
| 2-Octanol | 1.9 |
| Phenethyl alcohol | 1.85 |
| 1-Undecanol | 1.75 |
| 1-Hexanol | 2.2 |
| Cyclopentanol | 2.1 |
| Cyclohexanol | 1.85 |
| 1-Pentanol | 2.25* |

*Data obtained in multiplate rectification column ethylene glycol, 1,2-butanediol, 1,3-butanediol, 1,4-butanediol, 2,3-butanediol, dipropylene glycol, 1,5-pentanediol, 3-methyl-2,4-pentanediol, 2-methyl-1,3-propanediol, 1,2,6-trihydroxyhexane, 2-hydroxyacetophenone, benzyl benzoate, butyl lactate, phenyl acetate, butyronitrile, methyl ethyl ketoxime, methyl isobutyl ketoxime, methyl n-amyl ketoxime, ethyl caproate, ethyl isovalerate, butyl aldehyde oxime, methyl valerate, methyl benzoate, benzonitrile, isopropyl lactate, isoamyl formate, butyl formate, butyl butyrate, tri-2-ethyl hexyl trimellitate, propylene carbonate, 2-undecanone, diisobutyl ketone, 2,6-dimethyl-4-heptanone, acetophenone, nitromethane, nitroethane, 1-nitropropane, 2-nitropropane, nitrobenzene, 2-nitrotoluene, 3-nitrotoluene, acetonitrile, butyronitrile, tridecyl alcohol, 1-decanol, isodecyl alcohol, 2-octanol, phenethyl alcohol, 1-undecanol, 1-hexanol, cyclopentanol, cyclohexanol and 1-pentanol.

THE USEFULNESS OF THE INVENTION

The usefulness or utility of this invention can be demonstrated by referring to the data presented in Tables 1,2 and 3. All of the successful agents show that methylene chloride can be separated from tetrahydrofuran by means of extractive distillation in a rectification column and the ease of separation as measured by relative volatility is considerable.

WORKING EXAMPLES

Example 1

1.5 grams of methylene chloride, 28.5 grams of tetrahydrofuran and 40 grams of 1,2-butanediol were charged to a vapor-liquid equilibrium still and refluxed for five hours. Analysis indicated a vapor composition of 5% methylene chloride, 95% tetrahydrofuran; a liquid composition of 2.3% methylene chloride, 97.7% tetrahydrofuran. This is a relative volatility of 2.2.

Example 2

A solution comprising 15 grams of methylene chloride and 150 grams of tetrahydrofuran was placed in the stillpot of a 5.6 theoretical plate glass perforated plate rectification column. When refluxing began, an extractive agent comprising 1-pentanol was pumped into the top of the column at a rate of 15 ml/min. The temperature of the extractive agent as it entered the column ws 60° C. After establishing the feed rate of the extractive agent, the heat input to the methylene chloride-tetrahydrofuran in the stillpot was adjusted to give a total reflux rate of 40 ml/min. Afer one hour of operation, overhead and bottoms samples were collected and analysed. The overhead composition was 77.4% methylene chloride, 22.6% tetrahydrofuran and the bottoms composition was 3.6% methylene chloride, 96.4% tetrahydrofuran. This gives a relative volatility of methylene chloride to tetrahydrofuran of 2.25 for each theoretical plate.

I claim:

1. A method for recovering methylene chloride from a mixture of methylene chloride and tetrahydrofuran which comprises distilling a mixture of methylene chloride and tetrahydrofuran in the presence of about one part by weight of an extractive agent per part of methylene chloride-tetrahydrofuran mixture, recovering the methylene chloride as overhead product and obtaining the tetrahydrofuran and the extractive agent as bottoms product, wherein said extractive agent consists of one material selected from the group consisting of ethylene glycol, 1,2-butanediol, 1,3-butanediol, 1,4-butanediol, 2,3-butanediol, dipropylene glycol, 1,5-pentanediol, 3-methyl-2,4-pentanediol, 2-methyl-1,3-propanediol, 1,2,6-trihydroxyhexane, 2-hydroxyacetophenone, benzyl benzoate, butyl lactate, phenyl acetate, butyronitrile, methyl ethyl ketoxime, methyl isobutyl ketoxime, methyl n-amyl ketoxime, ethyl caproate, ethyl isovalerate, butyl aldehyde oxime, methyl valerate, methyl benzoate, benzonitrile, isopropyl lactate, isoamyl formate, butyl formate, butyl butyrate, tri-2-ethyl hexyl trimellitate, propylene carbonate, 2-undecanone, diisobutyl ketone, 2,6-dimethyl-4-heptanone, acetophenone, nitro-methane, nitroethane, 1-nitropropane, 2-nitropropane, nitrobenzene, 2-nitrotoluene, 3-nitrotoluene, acetonitrile, butyronitrile, tridecyl alcohol, 1-decanol, isodecyl alcohol, 2-octanol, phenethyl alcohol, 1-undecanol, 1-hexanol, cyclopentanol, cyclohexanol and 1-pentanol.

* * * * *